(12) United States Patent
Mozaffari et al.

(10) Patent No.: US 11,524,091 B2
(45) Date of Patent: Dec. 13, 2022

(54) GILZ FORMULATIONS FOR WOUND HEALING

(71) Applicant: Augusta University Research Institute, Inc., Augusta, GA (US)

(72) Inventors: Mahmood Mozaffari, Martinez, GA (US); Babak Baban, Augusta, GA (US); Rafik Abdelsayed, Evans, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 0 days.

(21) Appl. No.: 16/541,252

(22) Filed: Aug. 15, 2019

(65) Prior Publication Data

US 2020/0061237 A1 Feb. 27, 2020

Related U.S. Application Data

(60) Provisional application No. 62/720,561, filed on Aug. 21, 2018.

(51) Int. Cl.
*A61L 26/00* (2006.01)
*A61K 38/17* (2006.01)
*C07K 14/47* (2006.01)

(52) U.S. Cl.
CPC ...... *A61L 26/0047* (2013.01); *A61K 38/1709* (2013.01); *C07K 14/4705* (2013.01)

(58) Field of Classification Search
None
See application file for complete search history.

(56) References Cited

U.S. PATENT DOCUMENTS

| | | | |
|---|---|---|---|
| 4,990,144 A | 2/1991 | Blott | |
| 5,147,338 A | 9/1992 | Lang | |
| 5,810,755 A | 9/1998 | Leveen | |
| 2003/0180302 A1* | 9/2003 | Wolf | A61K 48/00 424/146.1 |
| 2004/0194160 A1* | 9/2004 | Riccardi | C07K 14/4705 800/18 |
| 2005/0164906 A1* | 7/2005 | Riccardi | A61P 29/00 514/1.1 |

OTHER PUBLICATIONS

Latella et al., Curr Opin Gastroenterol. Jul. 2017 ; 33(4): 239-245. doi:10.1097/MOG.0000000000000363.*
Elliot et al., Journal of Investigative Dermatology, 138:736-740, 2018.*
Vago et al., The Journal of Immunology, 2015, 194: 4940-4950, doi: 10.4049/jimmunol.1401722.*
Deflino et al., Blood, 2004; 104:4134-4141.*
Kalafatovic et al., Molecules, 2017, 22, 1929; doi:10.3390/molecules22111929.*
Ayroldi, E. et al., "Glucocorticold-induced leucine zipper (GILZ): a new important mediator of glucocorticoid action," Faseb J, 23:3649-3658 (2009).
Baban, B. et al., "The role of GILZ in modulation of adaptive immunity in a murine model of myocardial infarction", Exp Mol Pathol 102(3):408-414 (2017).
Beaulieu, E. et al., "Glucocorticoid-induced leucine zipper is an endogenous anti-inflammatory mediator in arthritis", Arthritis Rheum, 62(9):2651-2661 (2010).
Bereschenko, O. et al., GILZ promotes production of peripherally induced Treg cells and mediates the crosstalk between glucocorticoids and TGF-beta signaling, Cell Rep, 7(2):464-475 (2014).
Cannarile, L. et al., "Glucocorticoid-induced leucine zipper is protective in Th1-mediated models of colitis," Gastroenterology, 136:530-541 (2009).
D'Adamio, F. et al., "A new dexamethasone-induced gene of the leucine zipper family protest T lymphocytes from TCR/CD3-activated cell death", Immunity 7(6):803-812 (1997).
Fan, H. et al., "Targeting side effect of steroid therapy in autoimmune diseases; The role of GILZ". Discov Med 13 (69):123-133 (2012).
Jones, S.A. et al., "GILZ regulates Th17 responses and restrains IL-17 mediated skin inflammation," J Autoimmun, 61:73-80 (2015).
Riccardi, C. et al., "Glucocorticoid hormone-induced modulation of gene expression and regulation of T-cell death: role of GITR and GILZ, two dexamethasone-induced genes," Cell Death Differ, 6(12):1182-1189 (1999).
Ronchetti, S. et al., "GILZ as a mediator of the anti-inflammatory effects of glucocorticoids", Front Endocrinol (Lausanne), 6:170 (2015).
Sen C.K. et al., Wound Repair and Regeneration, 17:763-771 (2009).
Srinivasan, M. et al., "Glucocorticoid-induced leucine zipper in central nervous system health and disease," Mol Neurobiol, 54(10):8063-8070 (2017).
Yang, N. et al., "Role of glucocorticoid-induced leucine zipper (GILZ) in inflammatory bone loss", PLoS One, 12(8): e0181133 (2017).

* cited by examiner

*Primary Examiner* — Marianne P Allen
(74) *Attorney, Agent, or Firm* — Smith, Gambrell & Russell; Judy Jarecki-Black (57) ABSTRACT

Glucocorticoid-induced leucine zipper protein (GILZ) peptide compositions and their methods of use in wound healing are disclosed herein. An exemplary GILZ peptide composition includes a GILZ fusion protein. The GILZ peptide compositions can be administered topically to wounds, for example in the form of a cream, ointment, or lotion. The GILZ peptide compositions can be used to treat acute wounds, induce wound healing in chronic wounds, and reduce scar formation.

11 Claims, 8 Drawing Sheets

Specification includes a Sequence Listing.

Mouse 2
4.5mm by 4mm right side = 18mm²
2mm by 3mm left side = 6mm²

Mouse 1
2mm by 4mm right side = 8mm $^2$
1.5mm by 3mm left side = 4.5mm $^2$

GILZ FORMULATIONS FOR WOUND HEALING

CROSS-REFERENCE TO RELATED APPLICATIONS

This application claims benefit of and priority to U.S. Provisional Patent Application No. 62/720,561 filed Aug. 21, 2018, which is incorporated by reference in its entirety.

REFERENCE TO SEQUENCE LISTING

The Sequence Listing submitted as a text file named "064466.100_seqlisting_ST25" created on Jul. 18, 2019, and having a size of 4, 939 bytes is hereby incorporated by reference pursuant to 37 C.F.R. § 1.52(e)(5).

TECHNICAL FIELD OF THE INVENTION

Aspects of this invention are generally related to compositions and methods of enhancing and inducing wound healing.

BACKGROUND OF THE INVENTION

The management of chronic wounds has become a major therapeutic challenge which will continue to escalate due to increasing incidence of conditions that impede healing such as diabetes, obesity, and vascular disease. Due to an aging population and an increased burden of both diabetes and obesity, the financial burden of treating chronic wounds has risen dramatically (Sen C K, et al., *Wound Repair and Regeneration,* 17:763-771 (2009). The lifetime probability of a diabetic developing a chronic foot or leg ulcer is between 10-25%. In addition, pressure ulcers in critical care and intensive care patients are also on the rise.

The primary objectives of wound healing include timely wound closure, prompt pain relief, and an aesthetically acceptable scar. Normal wound healing involves four temporally and spatially overlapping phases: hemostasis, inflammation, proliferation, and remodeling. Acute wounds that progress normally through the healing process tend to heal within three weeks. However, chronic wounds often stall in the inflammatory stage of the healing process and persist for a minimum of three months after the injury.

The current gold standard for the management of chronic wounds is split-thickness autograft wherein wound closure involves harvesting full thickness fascia from a donor site and grafting it over the compromised region. While this method reduces healing time for chronic wounds, there are a number of issues that can arise including scarring and contracture of the wound site and donor site morbidity and pain. Wound dressings represent another commonly utilized wound healing method. Wound dressings function to preserve hydration of the wound to optimize regeneration, protect against infection, and avoid disruption of the wound base. The most common issue with wound dressings is infection at the wound site. Therefore, there is a need for improved wound healing techniques to reduce healing time and infection.

It is an object of the disclosure to provide compositions and methods of their use thereof to enhance wound healing.

It is another object of the disclosure to provide compositions and methods of their use thereof to reduce scarring.

SUMMARY OF THE INVENTION

Compositions and methods of their use for promoting and enhancing wound healing are provided. One embodiment provides a method for promoting wound healing by administering to the wound a composition comprising the disclosed GILZ peptides or fusion proteins in an amount effective to reduce inflammation, promote wound healing, or both. The GILZ peptide can have an amino acid sequence having at least 75, 80, 85, 90, 95, 98, 99, or 100% sequence identity to any one of SEQ ID NOs:1-3. The GILZ peptide can be operably linked to a cell penetrating peptide that is selected from the group consisting of TAT, Penetratin, pVEC, Pep1, MPG, and polyarginine. The disclosed fusion proteins can be formulated into a pharmaceutical composition in combination with a pharmaceutically acceptable excipient. The GILZ peptides can be formulated for topical administration. Exemplary formulations include a cream, ointment, or spray. In another embodiment, the fusion peptides are formulated into a wound dressing.

In one embodiment, the disclosed compositions and methods can be used to treat skin or mucosal wounds. The wounds can be acute, chronic, or fibrotic. Acute wounds can be surgical wound, abrasions, incisions, lacerations, first degree burns, second degree burns, or third degree burns. Chronic wound can be venous leg ulcer, arterial leg ulcer, diabetic ulcer, or decubitus ulcer.

Another embodiment provides a method of treating non-healing wounds by administering to the wound a composition comprising GILZ peptide in an amount effective to induce wound healing in a non-healing wound.

One embodiment provides a method of reducing scar formation by administering to the wound the disclosed GILZ peptides in an amount effective to enhance wound healing and reduce scar formation, wherein the composition is administered to the wound daily for at least six weeks.

Another embodiment provides a method for reducing inflammation in a subject in need thereof by locally administering the disclosed GILZ peptide pharmaceutical compositions to a site of inflammation in an amount effective to reduce immune cells infiltrating into the site. The immune cells can be neutrophils.

BRIEF DESCRIPTION OF THE DRAWINGS

FIGS. 1B and 1D show wound sites of two representative mice at Day 0. FIGS. 1A and 1C show wound sites of two representative mice at Day 8.

DETAILED DESCRIPTION OF THE INVENTION

I. Definitions

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The terms "treat," "treating," "treatment" and "therapeutic use" refer to the elimination, reduction or amelioration of one or more symptoms of a disease or disorder. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

An "immune cell" refers to any cell from the hemopoietic origin including, but not limited to, T cells, B cells, monocytes, dendritic cells, antigen presenting cells, and macrophages.

The term "inflammatory molecules" refer to molecules that result in inflammatory responses including, but not limited to, cytokines and metalloproteases such as including, but not limited to, IL-1β, TNF-α, TGF-beta, IFN-γ, IL-18, IL-17, IL-6, IL-23, IL-22, IL-21, and MMPs.

The terms "immunologic," "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II MEW molecules to activate antigen-specific CD4+ T helper cells and/or CD8+ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays (CD4+ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

The terms "individual", "host", "subject", and "patient" are used interchangeably herein, and refer to a mammal, including, but not limited to, humans, rodents, such as mice and rats, and other laboratory animals.

The terms "wound" and "lesion" can be used interchangeably and refer to an injury to living tissue.

The terms "wound healing" and "wound repair" can be used interchangeably and refer to the process by which tissues repair themselves after injury. Wound healing is a complex, ordered process that is tightly controlled by multiple cell types that secrete growth factors, cytokines, and chemokines to promote closure and functional restoration of the barrier. Wound healing occurs through four temporally and spatially overlapping phases: hemostasis, inflammation, proliferation, and remodeling. Early stages of wound healing involve hemostasis and activation of keratinocytes and inflammatory cells. The intermediate stages involve proliferation and migration of keratinocytes, proliferation of fibroblasts, matrix deposition, and angiogenesis. Late-stage healing involves remodeling of the extracellular matrix (ECM) resulting in scar formation and restoration of the barrier.

The term "acute wound" refers to a wound that occurs suddenly rather than over time and heals at a predictable and expected rate according to normal wound healing process. Acute wounds typically develop after surgery or trauma. Types of acute wounds include but are not limited to lacerations, abrasions, punctures, incisions, gunshots, and burns.

The term "chronic wound" refers to barrier defects that have not proceeded through the wound healing process to regain structural and functional integrity. Chronic wounds often stall in the inflammatory phase of healing. The major causes of chronic wound formation include but are not limited to vascular insufficiency, diabetes mellitus, local-pressure effects, compromised nutritional or immunological status, advanced age, and chronic mechanical stress. The most common types of chronic wounds are diabetic foot ulcers, pressure ulcers, and venous stasis ulcers. Chronic wounds are characterized by a chronically inflamed wound bed and a failure to heal. These types of wounds represent a major challenge for patients and caregivers and require medical intervention unlike acute wounds which typically heal on their own.

"Scarring" refers to the physiological endpoint of wound repair. A scar is an area of fibrous tissue that replaces normal skin after an injury.

As used herein, "fibrosis" refers to the replacement of the normal structural elements of the tissue by distorted, non-functional and excessive accumulation of scar tissue. "Fibrotic wounds" are wounds that exhibit fibrosis and excess scarring.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

II. Compositions and Methods to Enhance Wound Healing

Compositions and methods of their use for wound healing and regeneration are provided. It has been discovered that glucocorticoid-induced leucine zipper protein (GILZ) peptides can promote and enhance wound healing. One embodiment provides a method to promote or enhance wound healing in a subject in need thereof by administering to the wound a composition containing an effective amount of GILZ peptide to promote or enhance healing of the wound. In some embodiments, the GILZ peptide is part of a fusion protein. The fusion protein or the GILZ peptide can also include a cell penetrating peptide to promote or enhance cellular uptake of the GILZ peptide or fusion protein. The disclosed peptide compositions can be applied to the wound topically. In one embodiment, the topical formulation can be a liquid, gel, cream, ointment, or paste.

A. Glucocorticoid-Induced Leucine Zipper Protein (GILZ)

Glucocorticoids are one of the most utilized anti-inflammatory drugs because of their strong effects on cells of the immune system. However, glucocorticoids also exhibit detrimental side effects including but not limited to steroid-induced osteoporosis, myopathy, avascular necrosis, hypertension, hyperglycemia, weight gain and obesity, behavioral/cognitive changes, gastritis, peptic ulcers, gastrointestinal hemorrhage, glaucoma, and cataracts. These side effects limit the therapeutic application of glucocorticoids.

Glucocorticoid-induced leucine zipper protein (GILZ) has been discovered to be a pivotal mediator of the anti-inflammatory effects of glucocorticoids. GILZ is a glucocorticoid-induced transcriptional regulatory protein. GILZ can homo- and hetero-dimerize with transcription factors such as NF-κB, Raf-1, TORC2, AP-1, Ras, and C/EBP, all of which are known to play a role in pro-inflammatory signaling. Other names for GILZ include but are not limited to tuberculosis sclerosis complex 22 (TCS22), DSIP-immunoreactive peptide, delta sleep-inducing peptide immunoreactor, TSC-22-like protein, and TSC-22 related protein.

GILZ has emerged as a possible alternative to glucocorticoid therapies, due to its anti-inflammatory actions which are not accompanied by glucocorticoid adverse effects. GILZ appears to have a physiological role in the regulation of inflammatory mechanisms; however, there are no reports on its applicability to wound regeneration and repair.

1. Peptides

Sequences for human GILZ are known in the art. For example, the consensus amino acid sequence of GILZ is as follows:

```
                                         (SEQ ID NO: 1)
UniProt Q99576-1 which has been incorporated
by reference in its entirety.
         10         20         30         40
MNTEMYQTPM EVAVYQLHNF SISFFSSLLG GDVVSVKLDN 50         60         70         80
SASGASVVAI DNKIEQAMDL VKNHLMYAVR EEVEILKEQI 90        100        110        120
RELVEKNSQL ERENTLLKTL ASPEQLEKFQ SCLSPEEPAP

130
ESPQVPEAPG GSAV
```

One embodiment provides an isolated or synthetic peptide, comprising an amino acid sequence having at least 75, 80, 85, 90, 95, 98, 99, or 100% sequence identity to SEQ ID NO: 1, optionally operatively linked to a cell penetrating peptide.

Another embodiment provides an isolated or synthetic peptide, comprising an amino acid sequence having at least 75, 80, 85, 90, 95, 98, 99, or 100% sequence identity to: MAQSKLDCRSPVGLDCCNCCLDLAHRSGLQRGSS- GENNNPGSPTVSNFRQLQEKLVFE NLNTDKLN-
SIMRQDSLEPVLRDPCYLINEGICNRNIDQTMLSILL-
FFHSASGASVVAIDNK
IEQAMDLVKNHLMYAVREEVEILKEQIRE-
LVEKNSQLERENTLLKTLASPEQLEKFQSCL S
PEEPAPESPQVPEAPGGSAV (SEQ ID NO:2) optionally
operably linked to a cell penetrating peptide.

Another embodiment provides an isolated or synthetic peptide, comprising an amino acid sequence having at least 75, 80, 85, 90, 95, 98, 99, or 100% sequence identity to: GGWPSAVRAWEKAGSLPAEKEFLASFRAGAS-
GASVVAIDNKIEQAMDLVKNHLMYAV REEVEIL-
KEQIRELVEKNSQLERENTLLKTLASPEQLEKFQSCL-
SPEEPAPESPQVPEAPGG SAV (SEQ ID NO:3) optionally operably linked to a cell penetrating peptide.

The peptide compositions can include non-naturally occurring peptides and peptide mimetics. The peptides can be any amino acid sequence that is identical to the entire sequence or a fragment of GILZ peptide. The peptides can vary in length. The peptides can be 5, 10, 15, 20, 25, 30, 35, 40, 45, 50 or 100 amino acids in length. Typically peptides will be in the range of 5-200 amino acids in length.

The disclosed peptides can be modified. As an example, a "methylated derivative" of a peptide refers to a form of the peptide that is methylated. Unless the context indicates otherwise, reference to a methylated derivative of a peptide does not include any modification to the base peptide other than methylation. Methylated derivatives can also have other modifications, but such modifications generally will be noted. For example, conservative variants of an amino acid sequence would include conservative amino acid substitutions of the based amino acid sequence. Thus, reference to, for example, a "methylated derivative" of a specific amino acid sequence "and conservative variants thereof" would include methylated forms of the specific amino acid sequence and methylated forms of the conservative variants of the specific amino acid sequence, but not any other modifications of derivations.

Variants and derivatives are well understood by those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure.

As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity. Conservative variants are also referred to herein as "conservative amino acid substitutions," "conservative amino acid variants," "conservative substitutions," and similar phrase. A "conservative derivative" of a reference sequence refers to an amino acid sequence that differs from the reference sequences only in conservative substitutions.

As an example, a conservative variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative variant also can be a sequence in which a first basic amino acid is conservatively substituted with a second basic amino acid such as arginine, lysine, histidine, 5-hydroxylysine, N-methyllysine or an analog thereof. Similarly, a conservative variant can be a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative variant can be a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof. For example, the replacement of one amino acid residue with another that is biologically and/or chemically similar is known to those skilled in the art as a conservative substitution. For example, a conservative substitution would be replacing one hydrophobic residue for another or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein. It is understood that conservative variants of the disclosed amino acid sequences can encompass sequences containing, for example, one, two, three, four or more amino acid substitutions relative to the reference sequence, and that such variants can include naturally and non-naturally occurring amino acid analogs.

2. Fusion Protein

In another embodiment, the GILZ peptide is contained in a fusion protein. The GILZ peptide according to SEQ ID NO:1-3 can be coupled to other polypeptides to form fusion proteins. Fusion polypeptides have a first fusion partner including all or a part of a human GILZ peptide fused to a second polypeptide directly or via a linker peptide sequence that is fused to the second polypeptide. In one embodiment, GILZ peptide is fused to a second polypeptide. The fusion proteins optionally contain a domain that functions to dimerize or multimerize two or more fusion proteins. The peptide/polypeptide linker domain can either be a separate domain, or alternatively can be contained within one of the other domains (first polypeptide or second polypeptide) of the fusion protein. Similarly, the domain that functions to dimerize or multimerize the fusion proteins can either be a separate domain, or alternatively can be contained within one of the other domains (first polypeptide, second polypeptide or peptide/polypeptide linker domain) of the fusion protein. In one embodiment, the dimerization/multimerization domain and the peptide/polypeptide linker domain are the same.

Fusion proteins disclosed herein are of formula I:

wherein "N" represents the N-terminus of the fusion protein, "C" represents the C-terminus of the fusion protein, "$R_1$" is a GILZ peptide, or functional variant or fragment thereof, "$R_2$" is an optional peptide/polypeptide linker domain, and "$R_3$" is a second polypeptide. In one embodiment, the second peptide is a cell penetrating peptide, for example a TAT peptide. Alternatively, $R_3$ is the GILZ peptide, or functional variant or fragment thereof and $R_1$ is the second polypeptide.

3. Cell Penetrating Peptides:

In some embodiments, the efficacy of GILZ peptides is enhanced by conjugating the peptide to a cell penetrating peptide. Cell penetrating peptides are short amino acid sequences that are able to traverse biological membranes and deliver small molecules, proteins, viruses, and drugs inside of cells. In one embodiment, the cell penetrating peptides are 5-30 residues long. Cell penetrating peptides are classified as either protein derived cell penetrating proteins, chimeric cell penetrating proteins, or synthetic cell penetrating peptides.

Human immunodeficiency virus I (HIV 1) trans-activating protein (Tat) is a commonly utilized protein derived cell penetrating peptide. The α-helical domain of Tat protein spanning the residues 48 to 60 was found as the main determinant for cell internalization and nucleus translocation. Numerous cell penetrating peptides have been derived from the Tat dodecapeptide GRKKRRQRRRPQ (SEQ ID NO:4). Another common protein derived cell penetrating peptide is Penetratin peptide which has an amino acid sequence RQIKIWFQNRRMKWKK (SEQ ID NO:5).

Exemplary cell penetrating peptides include but are not limited to, YTA2, YTA4, TAT, Pen, R12, R16, r8, r12, R5, R7, Glu-Oct-6, Glu-Lys, 6-Oct, Phe-Oct-6, Asn-Oct-6, Tyr-Oct-6, RV24, TAT-NBD, TMTP1-TAT-NBD, AgNP-TAT, crotamine, R9-GO-203, iRGD-CDD, P7-1, P7-5, P7-6, P7-7, R7-KLA, KLA-R7, P1, P2, P3, P4, MG2A, CRGDK, L1, oligoarginine, GC/R8-Lip, p21-ELP1-Bac, Bac-ELP43, BacELP63, Bac-ELP122, TP10-SRC1LXXLL, R7-SRC1LXXLL, TP10-SRC1(1222-1245), R7-SRC1 (1222-1245), pep5-cpp, N-pep5-cpp, N2-pep5-cpp, N3-pep5-cpp, C2-pep5-cpp, C3-pep5-cpp, C4-pep5-cpp, C5-pep5-cpp, C6-pep5-cpp, C7-pep5-cpp, Ac-pep5-cpp, C24-LMWP, TAT-gelonin, TAT-BID, PTX-TAT-LP, PTX-C-TAT-LP, PTX-N-TAT-LP, B1, B1-Leu, B1-Lys, TAT-LP-PTX, T7/TAT-LP-PTX, T7-LP, TP, TP-biot1, TP-biot13, TP-10, TP10-biot1, P28, RALA peptide, TAT(47-57), Penetratin, pVEC, PEP-1, DS4.3, SR9, HR9, PR9, pf14, d-NTD, q-NTD, TH, MPG, polyarginine, SAP, CyLoP-1, GALA, CADY, L17E, and MPPs.

Chemical modifications to cell penetrating peptides can enhance therapeutic delivery. Synthetic cell penetrating peptides can be generated with chemical modifications to improve cellular uptake and provide cellular and sub-cellular specific targeting. Exemplary modifications include but are not limited to replacement of lysines with ornithine residues to confer resistance to cellular degradation, modification of the structure of peptides into dendrimers or cyclization, addition of phosphorylated groups and hydrophobic moieties to improve stability, and introduction of D-amino acids instead of L-amino acid configuration to protect peptides from degradation.

In one embodiment, a fusion protein obtained by fusion of GILZ with a cell penetrating peptide facilitates penetration of the fusion protein into cells so that their administration can modify cell functions in vivo. In a preferred embodiment, the fusion protein contains GILZ peptide (any one of SEQ ID NOs:1-3) fused to TAT peptide (SEQ ID NO:4). Methods of making TAT-GILZ fusion proteins are known in the art. For example, TAT-GILZ fusion protein can be constructed by inserting GILZ cDNA in the TAT-C vector to produce an in-frame fusion protein. See for example Cannarile, L., et al., *Gastroenterology*, 136:530-541 (2009).

4. Vectors

Vectors encoding the proteins, polypeptides, fragments, variants and fusions thereof are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

An expression vector can include a tag sequence. Tag sequences, are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, Conn.), maltose E binding protein and protein A. In one embodiment, a nucleic acid molecule encoding one of the disclosed polypeptides is present in a vector containing nucleic acids that encode one or more domains of an Ig heavy chain constant region, for example, having an amino acid sequence corresponding to the hinge, $C_H2$ and $C_H3$ regions of a human immunoglobulin Cγ1 chain.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the proteins, polypeptides, fragments, variants and fusions thereof described herein.

The vectors described can be used to express the proteins, polypeptides, fragments, variants and fusions thereof in cells. An exemplary vector includes, but is not limited to, an adenoviral vector. One approach includes nucleic acid transfer into primary cells in culture followed by autologous transplantation of the ex vivo transformed cells into the host, either systemically or into a particular organ or tissue. Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In one embodiment, expression vectors containing nucleic acids encoding fusion proteins are transfected into cells that are administered to a subject in need thereof.

In vivo nucleic acid therapy can be accomplished by direct transfer of a functionally active DNA into mammalian somatic tissue or organ in vivo. For example, nucleic acids encoding polypeptides disclosed herein can be administered directly to lymphoid tissues. Alternatively, lymphoid tissue specific targeting can be achieved using lymphoid tissue-specific transcriptional regulatory elements (TREs) such as a B lymphocyte-, T lymphocyte-, or dendritic cell-specific TRE. Lymphoid tissue specific TREs are known in the art.

Nucleic acids may also be administered in vivo by viral means. Nucleic acid molecules encoding fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors.

Nucleic acids may also be delivered by other carriers, including liposomes, polymeric micro- and nanoparticles and polycations such as asialoglycoprotein/polylysine.

In addition to virus- and carrier-mediated gene transfer in vivo, physical means well-known in the art can be used for direct transfer of DNA, including administration of plasmid DNA and particle-bombardment mediated gene transfer.

B. Pharmaceutical Compositions

Pharmaceutical compositions containing the disclosed GILZ peptides are provided. Pharmaceutical unit dosage forms of GILZ peptides are suitable for mucosal (e.g., nasal, sublingual, vaginal, buccal, or rectal), topical, or transdermal administration to a patient. Examples of dosage forms include, but are not limited to: ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs.

Topical dosage forms of disclosed GILZ peptides include, but are not limited to, liquids, creams, lotions, ointments, gels, waxes, pastes, sprays, aerosols, solutions, emulsions, and other forms know to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). In a preferred embodiment, the disclosed modified GILZ peptides are delivered to skin or mucosal wound tissue in a suitable topical dosage form.

For non-sprayable topical dosage forms, viscous to semi-solid or solid forms including a carrier or one or more excipients compatible with topical application and having a dynamic viscosity preferably greater than water are typically employed. Suitable formulations include, without limitation, solutions, suspensions, emulsions, creams, ointments, powders, gels, waxes, pastes, liniments, salves, and the like, which are, if desired, sterilized or mixed with auxiliary agents (e.g., preservatives, stabilizers, wetting agents, buffers, or salts) for influencing various properties, such as, for example, osmotic pressure.

Transdermal and mucosal dosage forms of the compositions of the disclosure include, but are not limited to, ophthalmic solutions, patches, sprays, aerosols, creams, lotions, suppositories, ointments, gels, solutions, emulsions, suspensions, or other forms known to one of skill in the art. See, e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer the GILZ peptides of the disclosure include, but are not limited to, those disclosed in U.S. Pat. Nos. 4,624,665; 4,655,767; 4,687,481; 4,797,284; 4,810,499; 4,834,978; 4,877,618;

4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with pharmaceutically acceptable salts of a GILZ peptide of the disclosure. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The disclosed GILZ compositions can also be administered by intralesional injection. Intralesional injection allows for delivery of a medication directly into a specific skin lesion to treat local tissues with minimal systemic effects.

The exact amount of the compositions administered to a wound can vary from subject to subject, depending on the species, age, weight and general condition of the subject, the severity of the wound being treated, and the mode of administration. Thus, it is not possible to specify an exact amount for every composition. However, an appropriate amount can be determined by one of ordinary skill in the art using only routine experimentation given the teachings herein. Thus, effective dosages and schedules for administering the compositions may be determined empirically, and making such determinations is within the skill in the art.

For example, a typical daily dosage of a composition having a GILZ peptide used alone might range from about 1 µg/kg to up to 100 mg/kg of body weight or more per day, depending on the factors mentioned above. For example dosages can be about 0.01 to 5 mg/kg of the host body weight. In another embodiment, dosages can be 0.3 mg/kg body weight, 1 mg/kg body weight, 3 mg/kg body weight, 5 mg/kg body weight or 10 mg/kg body weight or within the range of 1-10 mg/kg body weight.

The application of topical formulations such as creams and ointments is often measured in fingertip units (FTUs). An FTU (about 500 mg) is the amount of medication needed to squeeze a line from the tip of an adult finger to the first crease of the finger. One FTU is enough to cover an area of skin the size of two adult hands with the fingers together. The recommended dosage will depend on what part of the body is being treated.

C. Wound Dressings

Wound dressings can be used to treat wounds in an attempt to stop bleeding, absorb exudates, and promote healing. Wounds are more susceptible to healing in a moist, clean, and warm environment. Wound dressings can provide protection to the periwound skin, form an effective bacterial barrier, and maintain the wound at an optimal temperature and pH. In one embodiment, the disclosed GILZ peptides can be applied to a wound before the wound is covered with a wound dressing. This can promote wound healing while protecting the wound from the external environment.

Exemplary types of wound dressings include but are not limited to gauze, bandages, transparent film, foam dressings, hydrogels, hydrocolloids, alginates, hydrofibers, and cloth wraps. In some embodiments, wound dressings can be impregnated with medication to aide in wound healing or treat infection. In one embodiment, wound dressings can be impregnated with the disclosed GILZ peptides. Methods of impregnating wound dressings are known in the art, for example U.S. Pat. Nos. 5,147,338, 4,990,144, and 5,810,755A.

D. Methods of Use

The compositions disclosed herein are useful in wound repair and healing. Compositions containing the disclosed GILZ peptide compositions can be used to enhance wound healing in acute wounds, promote wound healing in chronic wounds, and to reduce the formation of scars.

Without being bound to any one theory, it is believed that the disclosed GILZ peptides and compositions thereof are able to inhibit or reduce immune and inflammatory responses at the site of a wound, thereby reducing wound size and promoting wound healing. More specifically, it is believed that the application of GILZ peptide to the site of the wound reduces the amount of inflammatory cell infiltration into the wound tissue.

1. Treatment of Acute Wounds

In one embodiment, the GILZ peptide compositions disclosed herein are useful in the promotion of wound healing in acute wounds. Acute wounds typically occur from surgery or trauma and progress through the stages of healing within the predicted timeframe. In one embodiment, GILZ peptide compositions can be applied to acute wounds to promote or enhance healing. It is believed that promoting or enhancing wound healing can reduce the development of acute wounds.

In one embodiment, the disclosed GILZ peptide compositions are applied to surgical incisions intraoperatively. In another embodiment, the GILZ peptide composition is applied to the site of the surgical incision on a daily basis until the wound has healed. In one embodiment, the GILZ peptide composition is applied to the site of the wound once daily, twice daily, three times daily, or more than three times daily.

Acute wounds can include wounds to the skin or to mucosal surfaces including but not limited to the oral cavity and nasal sinuses. In another embodiment, the disclosed GILZ peptide compositions can be used intraoperatively to treat organ tissue wounds.

2. Treatment of Non-Healing Wounds

In another embodiment, the disclosed GILZ peptide compositions are useful in the promotion of wound healing in chronic wounds. Chronic wounds are wounds that do not progress through the stages of wound healing in a timely manner. Typically, wounds that have not healed within three months are considered chronic. Common chronic wounds include but are not limited to diabetic foot ulcers, venous leg ulcers, arterial leg ulcers, diabetic ulcers, and decubitus (pressure) ulcers. Additionally, surgical wounds can exhibit delayed healing in patients with comorbidities such as diabetes, obesity, and vascular disease.

The disclosed GILZ peptide compositions can be applied to chronic wounds to promote wound healing. Without being bound by any one theory, it is believed that chronic wounds stall in the inflammatory stage of wound repair. While regulated inflammation is conducive to wound healing, exacerbated inflammation worsens tissue injury. The disclosed GILZ peptide compositions can reduce tissue injury and promote reparative and regenerative mechanisms.

In one embodiment, the disclosed GILZ peptide compositions are applied to the chronic wound on a daily basis. The composition can be applied to the wound 1, 2, 3, or more than 3 times per day. In one embodiment, the GILZ peptide composition can be combined with other chronic wound treatments. Chronic wound treatments include but are not limited to wound dressing, antimicrobials, antibiotics, anti-inflammatory medication, wound debridement (surgical or enzymatic), stem cell therapy, and growth factors.

3. Reduction of Scar Formation

Scar formation is the physiological endpoint of normal wound healing. In healthy individuals, scarring begins to occur approximately 20 days after the injury. Initially the scar tissue is raised and red, however as the scar matures its blood supply decreases and it becomes flatter and paler. Abnormal scars, including but not limited to keloid scats and hypertrophic scars, can occur during scar formation. In one embodiment, the disclosed compositions and methods can be used to reduce scar formation in tissue. There is evidence that suggests that inflammation during wound healing is directly linked to the extent of scar formation. Without being bound to any one theory, it is believed that the disclosed GILZ peptide compositions reduce inflammation during wound healing which can reduce the extent of scarring. The compositions can be used to prevent the formation of a scar at the same time as promoting wound healing.

Alternatively, the compositions may be used for reducing or initiating regression of existing scars. In one embodiment, the GILZ peptide compositions can be applied to scar tissue on a daily basis. The GILZ peptide compositions can be applied to the scar tissue until the scar has become more aesthetically acceptable to the individual. In some embodiments, regression of existing scars includes reduction in red coloration and a flatter appearance. The GILZ peptide compositions can be applied for two weeks, three week, four week, five weeks, six weeks, seven weeks, eight weeks, or more than eight weeks.

4. Treatment of Inflammatory Skin Conditions

In another embodiment, the disclosed GILZ peptide compositions treat inflammatory skin conditions. Exemplary inflammatory skin conditions include but are not limited to eczema, atopic dermatitis, seborrheic dermatitis, contact dermatitis, urticaria, rosacea, dermatitis herpetiformis, lichen planus, and *Pityriasis rosea*. In one embodiment, the disclosed GILZ peptide compositions are applied to the affected areas of skin or mucosal membrane to relieve one or more symptoms of the skin condition. The compositions can be applied once daily, twice daily, three times daily, or more than three times daily.

EXAMPLES

Example 1: TAT-GILZ Application Reduces Wound Size

Materials and Methods

A murine model of wound healing was used for these studies. Briefly, two 4-mm skin lesions were created, under ketamine/xylazine anesthesia, on the skin of the animal using a punch biopsy instrument. The two-lesion model is ideal because the control substance (TAT) and the experimental/active agent (TAT-GILZ) can be applied to each site in the same animal thereby avoiding confounding influence of inter-animal variations.

For these studies, each peptide was reconstituted in PBS buffer followed by daily application of 1 µg in 10 µl of the formulation to each site for 8 days. Pictures of the wound sites were taken on the day of the surgery and at sacrifice to procure tissue samples for subsequent processing for histological examination and flow cytometry-based assays.

Results

Figure 1A:
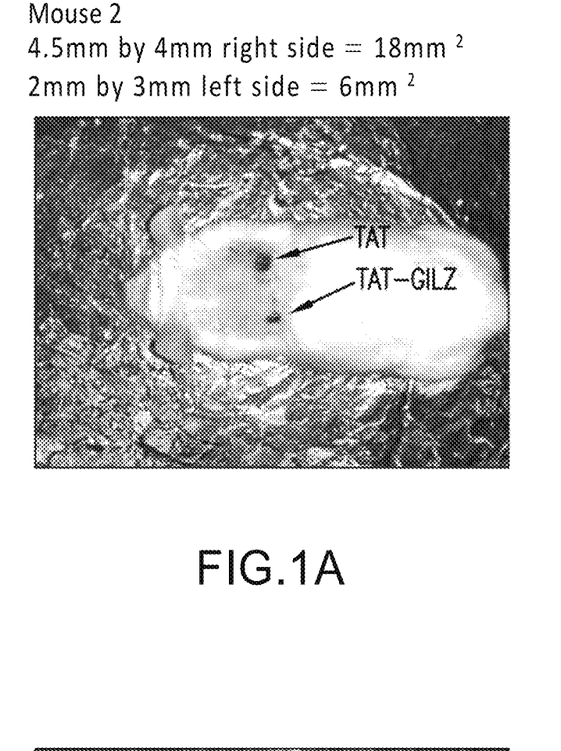
FIGS. 1A-1D are a panel of representative images of the clinical presentation of wound sites in mice with wounds treated with TAT or TAT-GILZ.
Figure 1B:
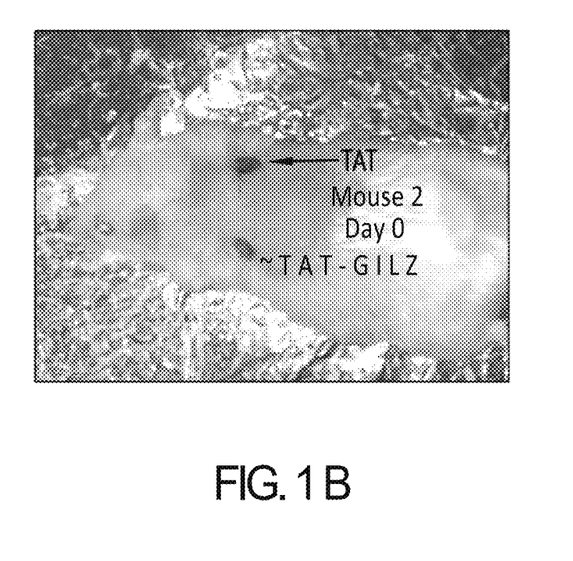
Figure 1C:
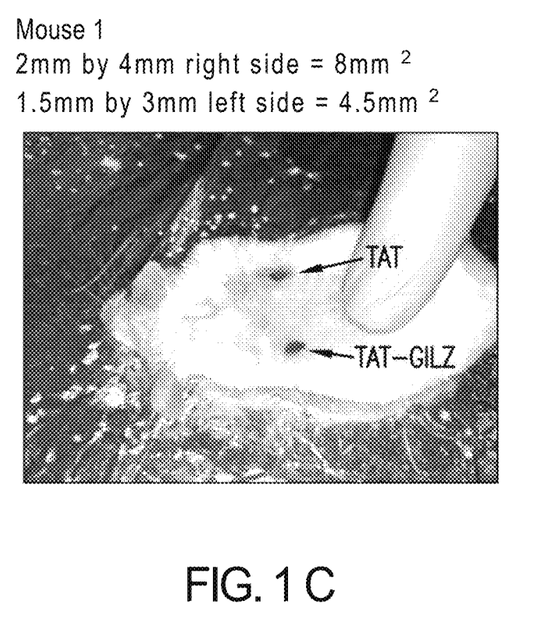
Figure 1D:
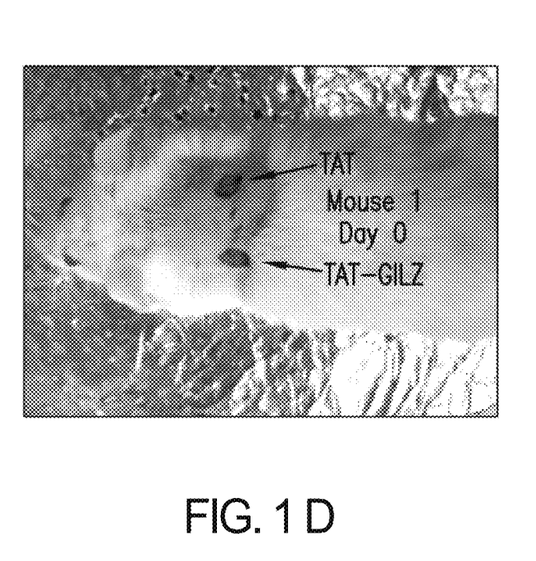

FIGS. 1A-1D show that the application of TAT-GILZ markedly reduced the wound size compared to TAT application.

Example 2: TAT-GILZ Application Reduces Inflammatory Responses

Methods

Skin wounds were subjected to histopathological examination using hematoxylin-eosin (H&E) and Mason Trichrome staining.

Results

Figure 2A:
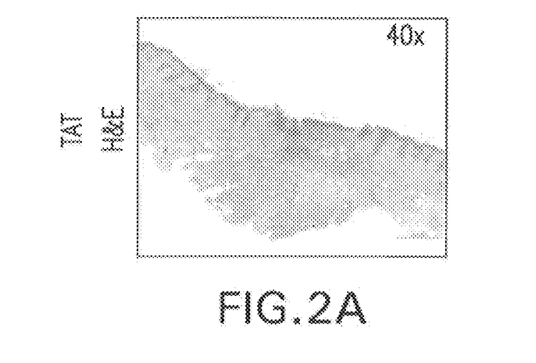
FIGS. 2A-2L are a panel of representative histological images of skin samples from lesion sites treated with either TAT (FIGS. 2A-2F) or TAT-GILZ (FIGS. 2G-2L). The skin samples were stained with H&E (FIGS. 2A-2C and 2G-2I) or Mason Trichrome (FIGS. 2D-2F and 2J-2L) and subjected to histological analysis.
Figure 2B:
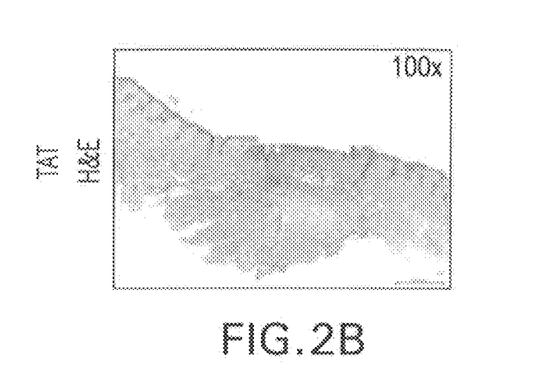
Figure 2C:
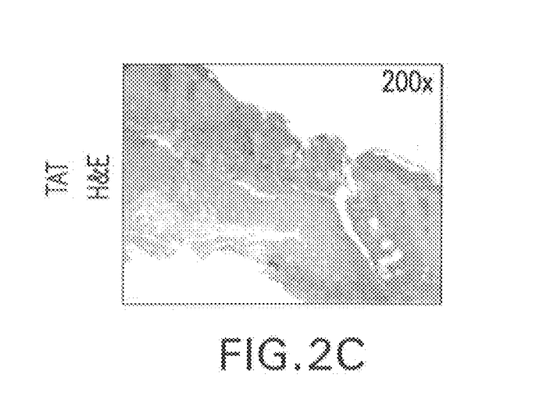
Figure 2D:
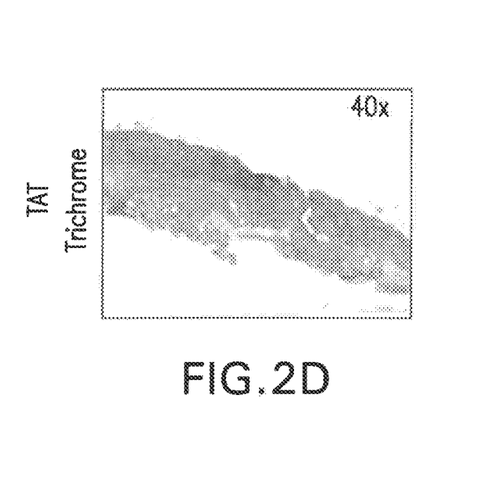
Figure 2E:
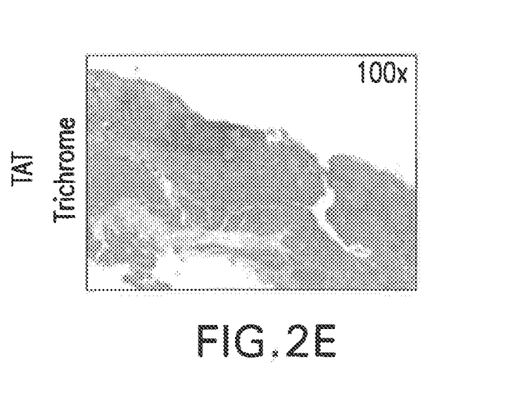
Figure 2F:
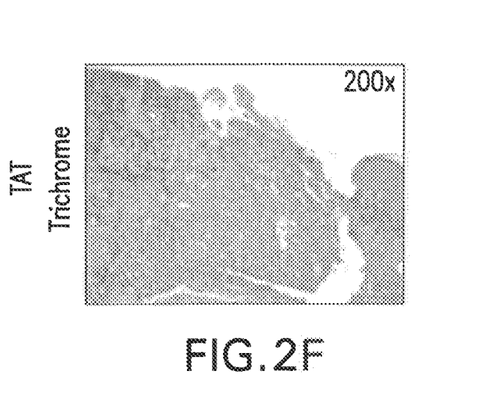

FIGS. 2A-2F show ulcerated skin lesions where the epidermis is discontinuous in the central region where it is replaced by granulation tissue surfaced by fibrin. The granulation tissue is composed of proliferation of myofibroblasts interspersed by sparse collagen and occasional small-sized blood vessels. Histopathological examination supports the interpretation of an intense inflammatory cell infiltrate, chiefly neutrophils, lymphocytes, and histiocytes in TAT-treated site. Trichrome staining revealed positive granulation tissue myofibroblasts with red cytoplasmic staining.

Figure 2G:
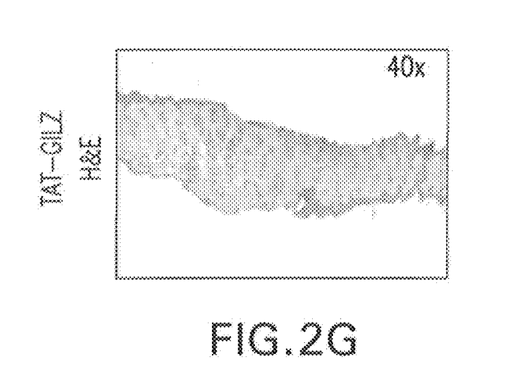
Figure 2H:
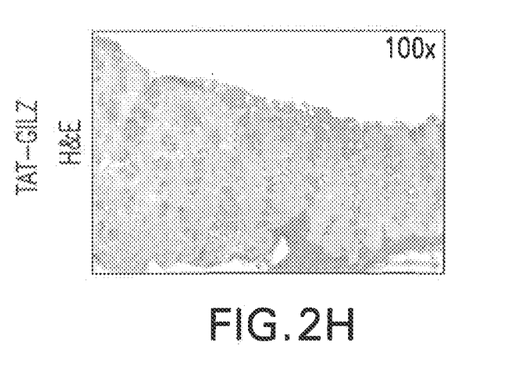
Figure 2I:
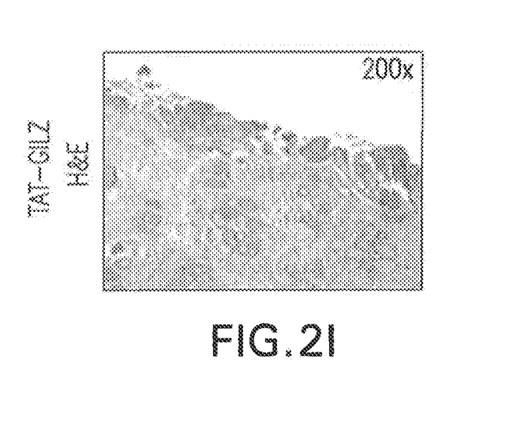
Figure 2J:
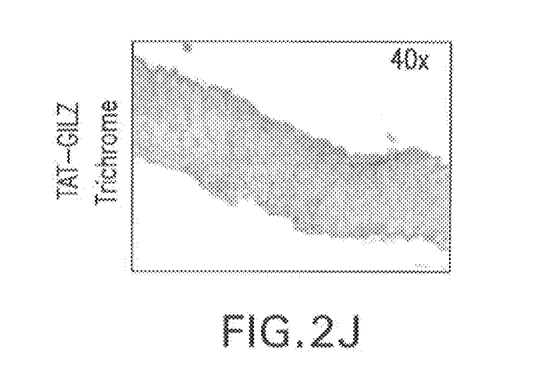
Figure 2K:
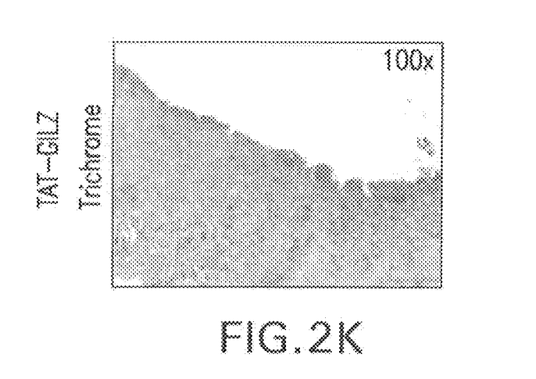
Figure 2L:
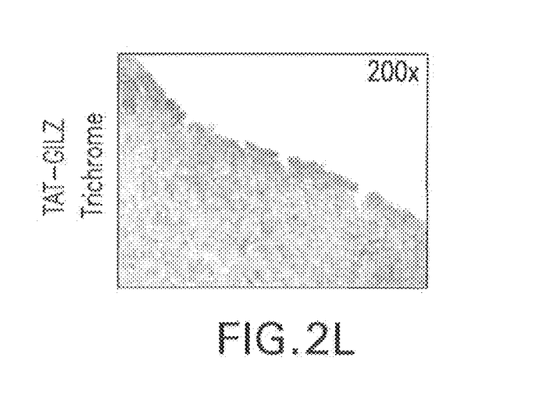

FIGS. 2G-2L show representative tissue sections from skin lesions treated with TAT-GILZ. Histological examination of ulcerated skin lesions where the epidermis is discontinuous in the central region revealed that it is replaced by granulation tissue surfaced by fibrin. The granulation tissue is composed of proliferation of myofibroblasts interspersed by sparse collagen and occasional small-sized blood vessels. Histological examination supports the interpretation of mild-moderate inflammatory cell infiltrate, chiefly neutrophils, lymphocytes, and histiocytes. The remainder of the specimen shows numerous regularly spaced pilosebaceous units, some of which appear in lower zones of the sections likely due to section orientation. Trichrome stain reveals positive granulation tissue myofibroblasts with red cytoplasmic staining.

Example 3: Effects of TAT-GILZ on Immune and Inflammatory Cells

Materials and Methods

To provide support for the histopathological observations, cells were prepared from wound sites and subjected to flow-cytometry-based analysis.

Results

Figure 3A:
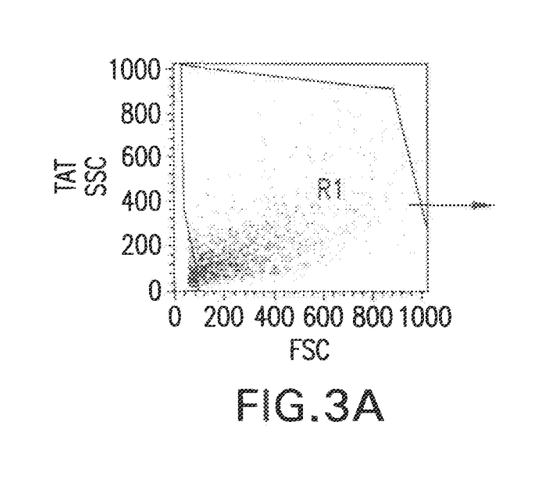
FIGS. 3A-3H are scatter plots from flow cytometry analysis of cells prepared from skin samples of experimental lesion sites treated with TAT (FIG. 3A-3D) or TAT-GILZ (FIG. 3E-3H). The proportion of regulatory/suppressive T lymphocytes (FIGS. 3A-3B and 3E-F) and neutrophils (FIGS. 3C-3D and 3G-3H) were determined in each treatment group.
Figure 3B:
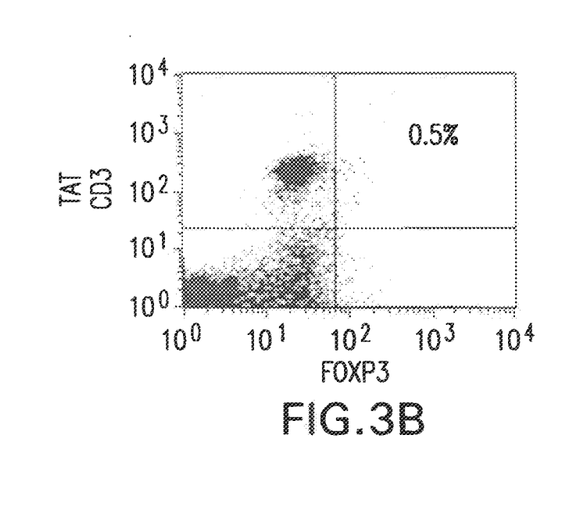
Figure 3C:
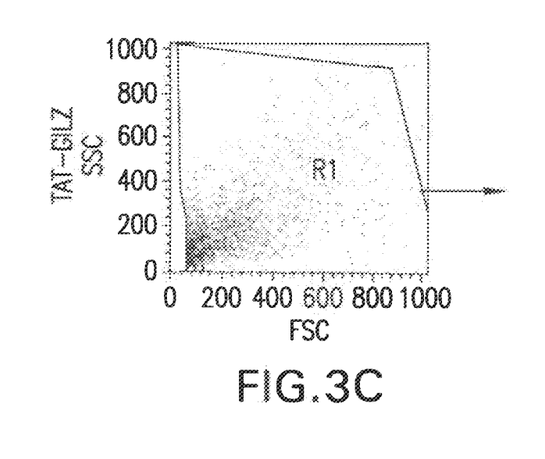
Figure 3D:
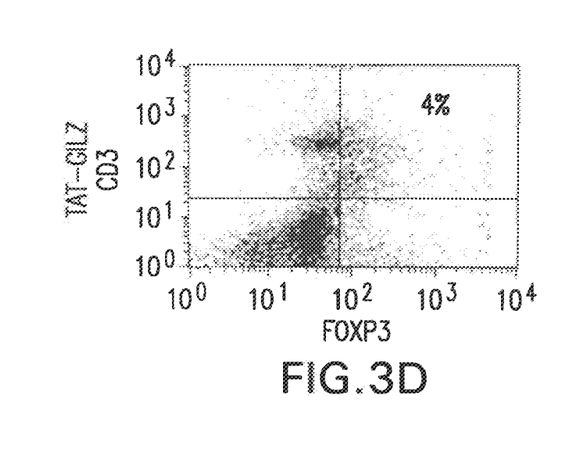
Figure 3E:
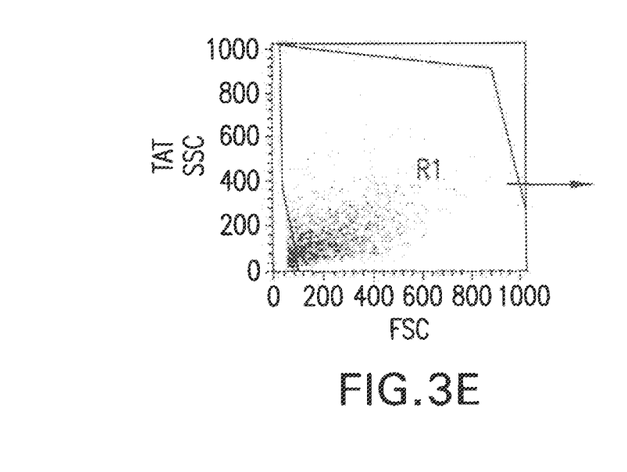
Figure 3F:
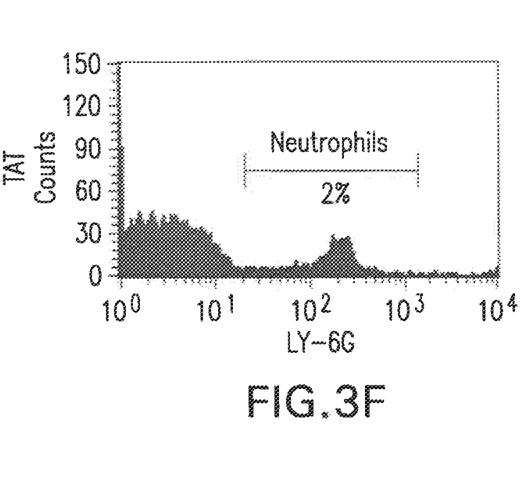
Figure 3G:
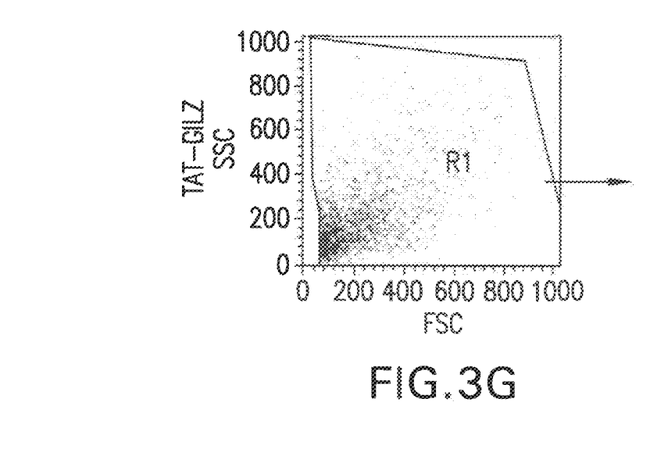
Figure 3H:
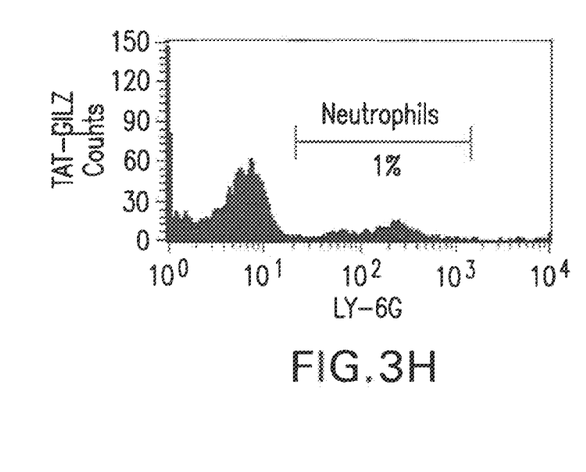

The proportion of CD3+/FOXP3+ cells was analyzed. CD3+/FOXP3+ cells are the flagship of suppressive adoptive immunity and are known to curtail inflammation. TAT-GILZ treatment markedly increased frequency of CD3+/FOXOP3+ cells compared to TAT treatment (FIGS. 3A-3B and 3E-3F). On the other hand, neutrophils are archetypal cells of innate immunity and their role in any inflammatory response is undeniable. As shown in FIGS. 3C-3D and 3G-3H, TAT-GILZ treatment was associated with reduction in neutrophil influx into the wound site compared to TAT.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method for promoting skin wound or lesion healing comprising, administering to the wound a composition comprising a GILZ peptide having 95, 98, 99, or 100% sequence identity to SEQ ID NO:1 fused to a cell penetrating peptide according to SEQ ID NO:4 in an amount effective to reduce inflammation and enhance wound healing.

2. The method of claim 1, wherein the skin wound or lesion is acute.

3. The method of claim 2, wherein the acute skin wound or lesion is selected from the group consisting of surgical wound, abrasions, incisions, lacerations, first degree burns, second degree burns, or third degree burns.

4. The method of claim 1, wherein the skin wound or lesion is chronic.

5. The method of claim 4, wherein the chronic skin wound or lesion is selected from the group consisting of venous leg ulcer, arterial leg ulcer, or decubitus ulcer.

6. The method of claim 1, wherein the skin wound or lesion is fibrotic.

7. A method of reducing scar formation in a skin wound or lesion comprising, administering to the wound a composition comprising a GILZ peptide having 95, 98, 99, or 100% sequence identity to SEQ ID NO:1 fused to a cell penetrating peptide according to SEQ ID NO:4 in an amount effective to enhance wound healing and reduce scar formation, wherein the composition is administered to the wound daily.

8. The method of claim 7, wherein the composition is formulated for topical administration.

9. The method of claim 8, wherein the topical composition is a cream, ointment, or spray.

10. The method of claim 7, wherein the composition is comprised in a wound dressing.

11. A method for reducing an inflammatory response at a site of a skin wound or lesion in a subject in need thereof, comprising:

locally administering a composition comprising a GILZ peptide having 99 or 100% sequence identity to SEQ ID NO:1 fused to a cell penetrating peptide according to SEQ ID NO:4 to a site of inflammation in an amount effective to reduce immune cells infiltrating into the site, wherein the immune cells comprise neutrophils, and wherein the site of inflammation is located at the site of the skin wound or lesion.

\* \* \* \* \*

SEQUENCE LISTING

```
<160> NUMBER OF SEQ ID NOS: 5

<210> SEQ ID NO 1
<211> LENGTH: 134
<212> TYPE: PRT
<213> ORGANISM: Homo sapiens

<400> SEQUENCE: 1

Met Asn Thr Glu Met Tyr Gln Thr Pro Met Glu Val Ala Val Tyr Gln
1               5                   10                  15

Leu His Asn Phe Ser Ile Ser Phe Phe Ser Ser Leu Leu Gly Gly Asp
            20                  25                  30

Val Val Ser Val Lys Leu Asp Asn Ser Ala Ser Gly Ala Ser Val Val
        35                  40                  45

Ala Ile Asp Asn Lys Ile Glu Gln Ala Met Asp Leu Val Lys Asn His
    50                  55                  60

Leu Met Tyr Ala Val Arg Glu Glu Val Glu Ile Leu Lys Glu Gln Ile
65                  70                  75                  80

Arg Glu Leu Val Glu Lys Asn Ser Gln Leu Glu Arg Glu Asn Thr Leu
                85                  90                  95

Leu Lys Thr Leu Ala Ser Pro Glu Gln Leu Glu Lys Phe Gln Ser Cys
            100                 105                 110

Leu Ser Pro Glu Glu Pro Ala Pro Glu Ser Pro Gln Val Pro Glu Ala
        115                 120                 125

Pro Gly Gly Ser Ala Val
    130

<210> SEQ ID NO 2
<211> LENGTH: 200
<212> TYPE: PRT
<213> ORGANISM: Artificial Sequence
<220> FEATURE:
<223> OTHER INFORMATION: Synthetic peptide

<400> SEQUENCE: 2

Met Ala Gln Ser Lys Leu Asp Cys Arg Ser Pro Val Gly Leu Asp Cys
1               5                   10                  15

Cys Asn Cys Cys Leu Asp Leu Ala His Arg Ser Gly Leu Gln Arg Gly
            20                  25                  30

Ser Ser Gly Glu Asn Asn Pro Gly Ser Pro Thr Val Ser Asn Phe
        35                  40                  45

Arg Gln Leu Gln Glu Lys Leu Val Phe Glu Asn Leu Asn Thr Asp Lys
    50                  55                  60

Leu Asn Ser Ile Met Arg Gln Asp Ser Leu Glu Pro Val Leu Arg Asp
65                  70                  75                  80
```

Pro Cys Tyr Leu Ile Asn Glu Gly Ile Cys Asn Arg Asn Ile Asp Gln
            85                  90                  95

Thr Met Leu Ser Ile Leu Leu Phe Phe His Ser Ala Ser Gly Ala Ser
        100                 105                 110

Val Val Ala Ile Asp Asn Lys Ile Glu Gln Ala Met Asp Leu Val Lys
        115                 120                 125

Asn His Leu Met Tyr Ala Val Arg Glu Glu Val Glu Ile Leu Lys Glu
    130                 135                 140

Gln Ile Arg Glu Leu Val Glu Lys Asn Ser Gln Leu Glu Arg Glu Asn
145                 150                 155                 160

Thr Leu Leu Lys Thr Leu Ala Ser Pro Glu Gln Leu Glu Lys Phe Gln
            165                 170                 175

Ser Cys Leu Ser Pro Glu Glu Pro Ala Pro Glu Ser Pro Gln Val Pro
            180                 185                 190

Glu Ala Pro Gly Gly Ser Ala Val
            195                 200

<210> SEQ ID NO 3
<211> LENGTH: 122
<212> TYPE: PRT
<213> ORGANISM: Artificial Sequence
<220> FEATURE:
<223> OTHER INFORMATION: Synthetic peptide

<400> SEQUENCE: 3

Gly Gly Trp Pro Ser Ala Val Arg Ala Trp Glu Lys Ala Gly Ser Leu
1               5                   10                  15

Pro Ala Glu Lys Glu Phe Leu Ala Ser Phe Arg Ala Gly Ala Ser Gly
            20                  25                  30

Ala Ser Val Val Ala Ile Asp Asn Lys Ile Glu Gln Ala Met Asp Leu
        35                  40                  45

Val Lys Asn His Leu Met Tyr Ala Val Arg Glu Glu Val Glu Ile Leu
    50                  55                  60

Lys Glu Gln Ile Arg Glu Leu Val Glu Lys Asn Ser Gln Leu Glu Arg
65                  70                  75                  80

Glu Asn Thr Leu Leu Lys Thr Leu Ala Ser Pro Glu Gln Leu Glu Lys
            85                  90                  95

Phe Gln Ser Cys Leu Ser Pro Glu Glu Pro Ala Pro Glu Ser Pro Gln
            100                 105                 110

Val Pro Glu Ala Pro Gly Gly Ser Ala Val
        115                 120

<210> SEQ ID NO 4
<211> LENGTH: 12
<212> TYPE: PRT
<213> ORGANISM: Human immunodeficiency virus type 1

<400> SEQUENCE: 4

Gly Arg Lys Lys Arg Gln Arg Arg Pro Gln
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Synthetic

<400> SEQUENCE: 5

-continued

```
Arg Gln Ile Lys Ile Trp Phe Gln Asn Arg Arg Met Lys Trp Lys Lys
1               5                   10                  15
```